United States Patent
Blaski et al.

(10) Patent No.: US 10,695,010 B2
(45) Date of Patent: Jun. 30, 2020

(54) APPARATUS AND METHOD FOR MAMMOGRAPHIC BREAST COMPRESSION

(71) Applicant: GENERAL ELECTRIC COMPANY, Schenectady, NY (US)

(72) Inventors: Ronald Blaski, Cedarburg, WI (US); Razvan Iordache, Paris (FR); Jerome Sutty, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 139 days.

(21) Appl. No.: 16/108,891

(22) Filed: Aug. 22, 2018

(65) Prior Publication Data
US 2020/0060632 A1  Feb. 27, 2020

(51) Int. Cl.
| | | |
|---|---|---|
| *A61B 6/04* | (2006.01) | |
| *A61B 6/00* | (2006.01) | |
| *A61B 5/00* | (2006.01) | |
| *G06T 7/00* | (2017.01) | |

(52) U.S. Cl.
CPC .......... *A61B 6/0414* (2013.01); *A61B 6/0435* (2013.01); *A61B 6/502* (2013.01); *A61B 6/544* (2013.01); *A61B 5/0053* (2013.01); *A61B 5/708* (2013.01); *G06T 7/0012* (2013.01); *G06T 2207/30068* (2013.01)

(58) Field of Classification Search
CPC ..... A61B 6/0414; A61B 6/0435; A61B 6/544; A61B 6/502; A61B 5/708; A61B 5/0053; G06T 2207/30068; G06T 7/0012
USPC .......................................................... 378/37
See application file for complete search history.

(56) References Cited

U.S. PATENT DOCUMENTS

| | | | |
|---|---|---|---|
| 9,050,009 B2 | 6/2015 | Den Heeten et al. | |
| 2010/0049093 A1 | 2/2010 | Galkin | |
| 2013/0028373 A1* | 1/2013 | Den Heeten | A61B 6/0414 |
| | | | 378/37 |
| 2014/0350358 A1 | 11/2014 | Oikawa | |

FOREIGN PATENT DOCUMENTS

EP   2536336 B1   6/2014

OTHER PUBLICATIONS

European patent application 19192419.0 filed Aug. 19, 2019; European Search Report dated Jan. 15, 2020; 9 pages.

(Continued)

*Primary Examiner* — David P Porta
*Assistant Examiner* — Gisselle M Gutierrez
(74) *Attorney, Agent, or Firm* — Grogan, Tuccillo & Vanderleeden, LLP

(57) ABSTRACT

A mammography apparatus includes a support plate for supporting a breast of a patient, a compression plate movable toward and away from the support plate for compressing the breast against the support plate, and a controller configured to control movement of the compression plate toward and away from the support plate. The controller is configured to adjust at least one of a rate of compression and a pressure applied to the breast based on a measurement of at least one of a diastolic pressure and a systolic pressure of the patient taken during at least one of a compression phase and a clamping phase of the mammography apparatus.

16 Claims, 5 Drawing Sheets

(56) References Cited

OTHER PUBLICATIONS

J E De Groot, et al: "A novel approach to mammographic breast compression: Improved standardization and reduced discomfort by controlling pressure instead of force.", Med Phys. Aug. 2013; 40(8): 081901, vol. 40, No. 8, Jul. 3, 2013 (Jul. 3, 2013), XP055654738; DOI: 10.1118/1.4812418.
Pain-preventing strategies in mammography: an observational study of simultaneously recorded pain and breast mechanics throughout the entire breast compression cycle published on Mar. 15, 2015 by Jerry E de Groot, et al.

\* cited by examiner

APPARATUS AND METHOD FOR MAMMOGRAPHIC BREAST COMPRESSION

BACKGROUND

Technical Field

Embodiments of the invention relate generally to mammographic imaging and, more particularly, to an apparatus and method for controlling and coordinating tissue compression during mammographic imaging.

Discussion of Art

The process of obtaining high quality mammographic images from breast tissue requires a technician to position the breast of a patient between one or more paddles that compress the breast in order to immobilize and flatten it during image acquisition. The compression force applied to a breast improves image quality by reducing the thickness of the breast while spreading the breast tissue over a larger area; this facilitates interpretation of obtained imagery since the amount of overlying tissue for structures within the imaged breast is minimized.

Reduction of the breast thickness by compression is also important in managing patient radiation dosage. In general, the thicker the compressed breast, the more x-ray attenuation. Therefore, a higher x-ray dosage is necessary when imaging thicker breast tissue as compared to the dosage required for thinner tissue. While greater compression forces are desirable for obtaining clear images with lower radiation dosages, greater compression forces may contribute to patient pain or discomfort. Such patients may not schedule or may delay any future examinations due to the fear of an uncomfortable procedure, thereby possibly increasing the risk that a serious medical condition may not be detected in a timely fashion.

Accordingly, some imaging systems have been developed that monitor and control the compression force applied to a patient's breast during mammographic imaging in an effort to minimize discomfort. Such systems, for example, may employ force sensors that measure the force applied to the breast to maintain the compression forces below certain predetermined thresholds. Depending on the patient, however, even compression forces below predetermined thresholds may cause pain or discomfort.

In view of the above, there is a need for an apparatus and method for controlling the compressive force applied to the breast of a patient during mammographic imaging that takes into account the physiology of each individual patient, to simultaneously reduce patient discomfort and enhance visualization of breast structures.

BRIEF SUMMARY OF THE INVENTION

In an embodiment, a mammography apparatus is provided. The mammography apparatus includes a support plate for supporting a breast of a patient, a compression plate movable toward and away from the support plate for compressing the breast against the support plate, and a controller configured to control movement of the compression plate toward and away from the support plate. The controller is configured to adjust at least one of a rate of compression and/or a pressure and/or compressive force applied to the breast based on a measurement of at least one of a diastolic pressure and/or a systolic pressure of the patient.

In another embodiment, a diagnostic imaging apparatus is provided. The apparatus includes a support plate for supporting tissue of a patient, a compression plate movable toward and away from the support plate for compressing the tissue against the support plate, and a controller configured to control movement of the compression plate toward and away from the support plate, and to adjust in real-time at least one of a rate of compression and/or a pressure applied to the tissue based on a measurement of a physiological parameter of a patient taken during at least one of a compression phase and/or a clamping phase of the apparatus.

In yet another embodiment, a method of operating a mammography apparatus is provided. The method includes the steps of positioning a breast of a patient on a support plate, moving a compression plate towards the support plate to compress the breast of a patient, measuring at least one of a diastolic pressure and/or a systolic pressure of a patient, and varying at least one of a rate of compression and/or a pressure applied to the breast based on the measurement of the at least one of the diastolic pressure and/or the systolic pressure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
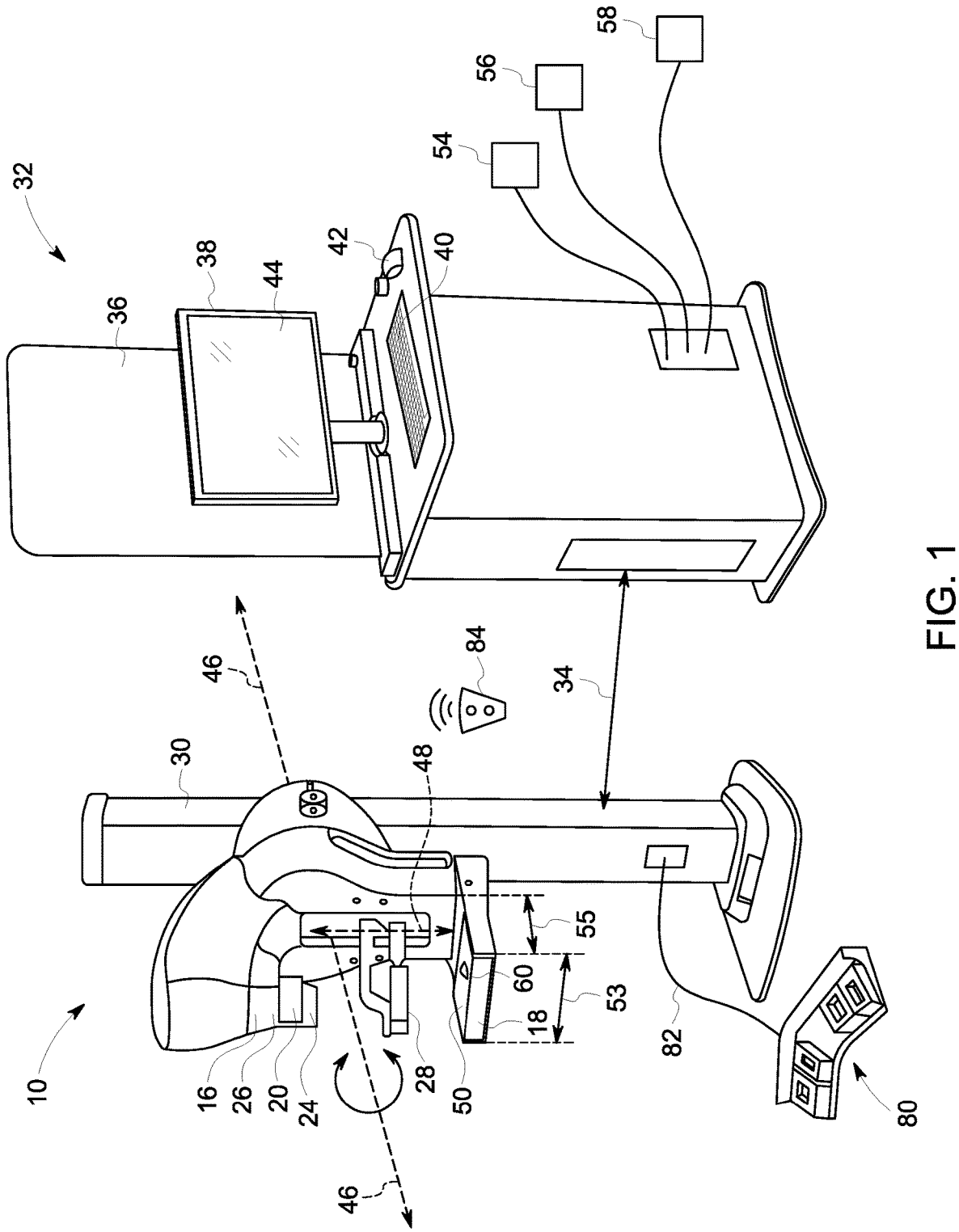
FIG. 1 is a perspective view of a mammography apparatus for imaging the breast tissue of a patient, in accordance with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to a mammography apparatus for the 2-dimensional imaging of breast tissue, it is to be understood that embodiments of the invention may be applicable to other types of imaging devices for both 2-dimensional and 3-dimensional imaging including, for example, digital breast tomosynthesis (DBT) and spectral mammography (single or multi-energy), as well as for imaging procedures for tissue other than breast tissue. Further still, embodiments of the invention may be used to analyze tissue, generally, and are not limited to analyzing human tissue.

Figure 2:
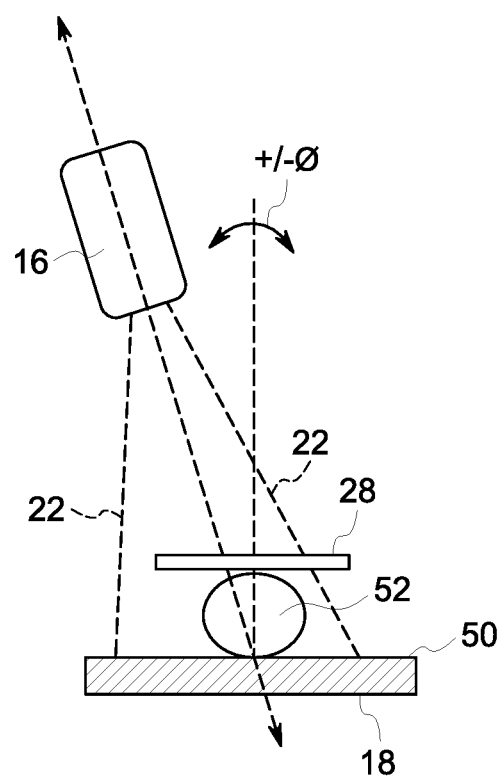
FIG. 2 diagram of the system of FIG. 1, showing the radiation source of the system in a scanning position, in accordance with an embodiment of the invention.

Referring now to FIGS. 1 and 2, the major components of a mammography system 10 for imaging breast tissue according to an embodiment of the invention are shown. The system 10 includes a radiation source/device 16, a radiation detector 18, and a collimator 20. The radiation source 16 is movable between a variety of imaging positions relative to the detector 18, and is operative to emit radiation rays 22 (FIG. 2) that are received by the radiation detector 18 to provide an image of a breast 52. In embodiments, the system 10 may include a patient shield 24 mounted to the radiation source 16 via face shield rails 26 to prevent the patient's head from obstructing the radiation rays and protecting the patient from the radiation rays 22.

Referring still further to FIGS. 1 and 2, the system 10 also includes a compression plate 28 and a support structure 30 to which one or more of the radiation source 16, radiation detector 18, and/or compression plate 28 may be mounted to. In embodiments, the system 10 may further include a controller 32. The controller 32 may be a workstation having at least one processor and a memory device as shown in FIG. 1 or, in other embodiments, the controller 32 may be embedded/integrated into one or more of the various components of the system 10 disclosed above. In embodiments, the controller 32 may be in electrical communication with the radiation source 16, radiation detector 18, and/or the compression plate 28 via a cable 34. As will be appreciated, in embodiments, the connection 34 may be a wireless connection. In embodiments, the controller 32 may include a radiation shield 36 that protects an operator of the system 10 from the radiation rays 22 emitted by the radiation source 16. The controller 32 may further include a display 38, a keyboard 40, mouse 42, and/or other appropriate user input devices that facilitate control of the system 10 via a user interface 44.

As further shown in FIGS. 1 and 2, the radiation source 16, along with the radiation detector 18, forms part of an x-ray system which provides x-ray imagery for the purpose of imaging a body part of a patient, such as breast 52. As stated above, the radiation source 16 emits the radiation rays 22 such that the radiation rays 22 travel from the radiation source 16 to the radiation detector 18. While the radiation rays 22 are discussed herein as being x-rays, it is to be understood that the radiation source 16 may emit other types of electromagnetic rays which can be used to image a patient. The radiation source 16 may be mounted to the support structure 30 such that the radiation source can rotate around an axis 46 in relation to the radiation detector 18, although movement of the radiation source 16 in paths other than rotation about a fixed axis, such as during digital breast tomosynthesis (DBT), are also envisioned. In embodiments, the radiation detector 18 may be configured to rotate or translate within its housing, such as in the directions indicated by arrows 53 and 55.

As stated above, the radiation detector 18 receives the radiation rays 22 emitted by the radiation source 16. In embodiments, data regarding the radiation rays 22 received by the radiation detector 18 may be electrically communicated to the controller 32 from the radiation detector 18 via cable/electronic connection 34 such that the controller 32 generates one or more images which may be shown on the display 38 and stored in the memory device.

The compression plate 28 is operative, in response to instruction from the controller 32 or in response to instructions from controller(s) on or near the mammography system 10 or switch controllers 80, to move towards and away from the radiation detector 18 as indicated by arrows 48 such that the compression plate 28 flattens and holds a body part, e.g., breast 52, in place against the surface 50 of the radiation detector 18. In this respect, the radiation detector 18 and the surface 50 thereof is referred to herein as a "support plate" that cooperates with the compression plate 28 to compress and clamp a breast of a patient therebetween.

Figure 3:
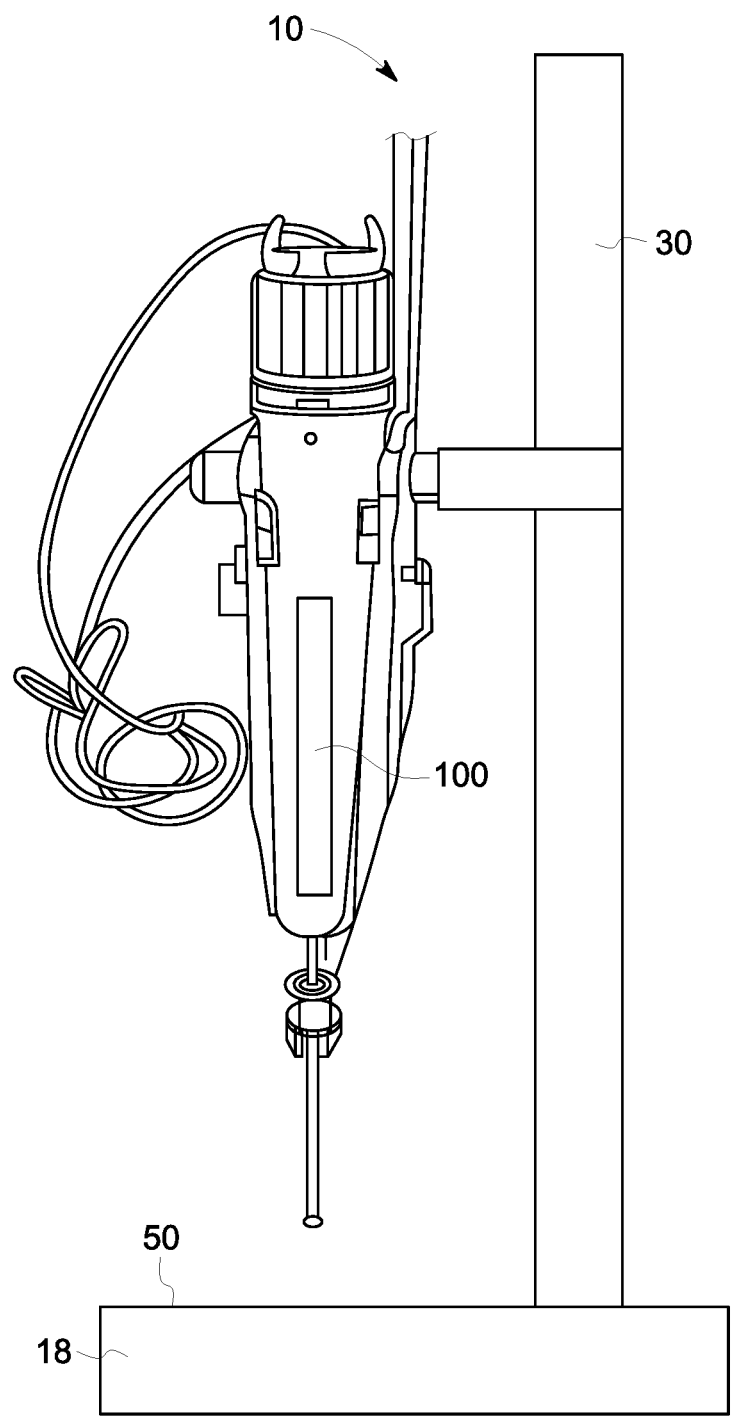
FIG. 3 is a perspective view of another embodiment of the system of FIG. 1 wherein the system includes a biopsy tool, in accordance with an embodiment of the invention.

In an embodiment, the system 10 may further, or alternatively, include a biopsy tool 100, illustrated in FIG. 3. In such an embodiment, the radiation source 16, along with the radiation detector 18, forms part of an x-ray system which provides x-ray imagery for the purpose of guiding the biopsy tool 100, e.g., needle, to a suspect site within a body part of a patient. As shown in FIG. 3, in embodiments, the biopsy tool 100, may be disposed on the support structure 30 such that it also rotates about the axis 46, in a manner similar to the radiation source 16, and/or moves in a vertical and/or horizontal direction, in a manner similar to the compression plate 28.

In operation, in accordance with an embodiment, the breast 52 of the patient may be placed onto the surface 50 of the radiation detector 18. The compression plate 28, under control of the controller 32, moves towards the detector 18 to compress the breast 52 against the surface 50 of the detector 18 such that the breast 52 is immobilized. Movement of the compression plate 28 towards the detector 18 to compress the breast 52 against the support plate/detector 18 defines a compression phase of the system 10. Once a target compression force is achieved, movement of the compression plate 28 is halted and the compression plate 28 and the support plate 18 are held in fixed position to clamp the breast 52 therebetween (referred to herein as the clamping phase) so that imaging or procedures, e.g., a biopsy, may be commenced. During an imaging procedure, the radiation source 16 is selectively adjusted such that it is moved/rotated to a first scanning position and scans the breast 52. The radiation detector 18 receives the radiation rays 22 passing through the breast 52 and sends data to the controller 32 which then generates one or more x-ray images of the breast 52. Once imaging is complete, the controller 32 moves the compression plate 28 away from the support plate 18 to free the breast 52.

Referring still further to FIG. 1, in an embodiment, the system 10 may include one or more physiological monitoring or sensor devices 54, 56, 58, 60 communicatively coupled with the controller 32 for monitoring one or more physiological parameters of a patient (and for transmitting physiological parameter data to the controller 32). While FIG. 1 illustrates that the sensor devices 54, 56, 58 are connected to the controller 32, in some embodiments, one or more of the sensor devices may be communicatively coupled with the mammography apparatus, without departing from the broader aspects of the invention. The sensor devices may be selected to monitor and/or measure any physiological information of a patient desired, including, but not limited to, diastolic blood pressure, systolic blood pressure, body temperature, blood oxygen level, patient weight, skin conductance, pulse rate, etc. As illustrated in FIG. 1, one or more of the sensor devices, e.g., sensor device 60, may be physically integrated with the compression plate 28 and/or the detector/support plate 18. By incorporating the sensor devices into the support plate 18 or compression plate 28, physiological parameter data of the patient may be acquired and transmitted to the controller 32 without requiring any additional intervention by the system operator.

In an embodiment, the sensor device 60 may be a force sensor for measuring the amount of pressure or compressive force applied to the breast 52. Additional sensors for measuring physiological parameters may be configured to either directly measure or allow the calculation of variables such as force, pressure, temperature, rigidity, elasticity, breast size and/or volume, and/or tissue density and could be embedded in compression plate 28 or support plate 18 or attached as part of mammography system 10.

The various sensor devices 54, 56, 58, 60 may be configured to acquire physiological parameter data from a patient during system operation. More specifically, physiological parameter data may be acquired continuously or at predetermined time intervals before breast compression and imaging, during the compression phase of the system and/or during the clamping phase of the system. In an embodiment, the physiological parameter data may be acquired continuously or at predetermined time intervals during at least the compression phase. In other embodiments, the physiological parameter data may be acquired continuously or at predetermined time intervals during at least the compression phase and the clamping phase.

In an embodiment, at least one of the sensor devices 54, 56, 58, 60 is a blood pressure measuring device configured to measure at least one of diastolic blood pressure and systolic blood pressure of a patient. For example, the blood pressure measuring device may be a blood pressure cuff configured for placement on the arm of a patient, an ultrasound device or a thermal imaging device. In an embodiment, the blood pressure measuring device may be integrated with at least one of the compression plate 28 and/or the support plate 18 (e.g., sensing device 60) for measuring the blood pressure of a patient directly from the patient's breast. As will be appreciated, the blood pressure measuring device may take continuous blood pressure measurements via pulse wave velocity measurements, continuous noninvasive arterial pressure methods and the like, and is not limited to any particular technique, method or apparatus.

In operation, the controller 32 is configured to control movement of the compression plate 28 toward the support plate 18 to flatten the breast 52 during the compression phase, and to clamp the breast 52 during the clamping phase, as discussed above. The controller 32 is also configured to control movement of the compression plate 28 to adjust at least one of a rate of compression and/or a pressure or compressive force applied to the breast 52 in response to the physiological parameter data acquired from the patient. For example, in an embodiment, the controller 32 is configured to vary the at least one of the rate of compression and/or the pressure applied to the breast 52 during the compression phase and/or clamping phase based on a measurement of at least one of a diastolic pressure and/or a systolic pressure of the patient taken during the compression phase and/or the clamping phase.

In particular, in embodiments where blood pressure is measured continuously during the compression phase and the clamping phase, the controller 32 may be configured to vary at least one of the rate of compression and/or the pressure applied in real-time, as practicable, as measured blood pressure changes. As used herein, "real-time" refers to a level of responsiveness that a user senses as sufficiently immediate, or that enables the controller (or other processor) to keep up with an external process, e.g., compression, pressure, etc. As used herein, "rate of compression" refers to the change in compressive force applied to the breast in relation to elapsed time. In an embodiment, at least one of the rate of compression and/or the pressure applied may be varied in real-time during the compression phase, and a target pressure has been reached for optimal image acquisition, the clamping phase may be initiated and the plates held in static position during the scan (2D, DBT, multi-energy, etc.). This ensures that the object being imaged remains in the same position during the scan.

In embodiments where blood pressure is measured at predetermined intervals during the compression phase and the clamping phase, the controller 32 may be configured to vary at least one of the rate of compression and/or the pressure applied after each measurement. In an embodiment, the real-time blood pressure measurements may be smoothed as a running average by the controller 32.

In an embodiment, the controller 32 is configured to vary at least one of the rate of compression and/or the pressure applied in based on measured blood pressure and one or more other physiological parameters such as, for example, a measured size or volume of the breast 52. The size or volume of the breast may be measured prior to commencing the procedure and input into the controller, or measured automatically using sensors integrated with the compression plate 28 and/or support plate 18.

In embodiments, a density or rigidity measurement and/or determination using one or more sensors integrated with the compression plate 28 and/or support plate 18 may be used by the controller 32 to determine when to cease compression during the compression phase. In particular, density or rigidity sensors may be utilized to determine when a target density or rigidity for optimal image quality is achieved, and the controller 32 may be configured to transition the system 10 from the compression phase to the clamping phase when a target tissue density and/or rigidity is achieved.

In the embodiments described above, at least one of the sensing devices may be configured to measure a physiological parameter that can be utilized by the controller 32 to determine whether or not blood is flowing in the compressed tissue. The controller 32 may be further configured to immediately cease and/or release compression on the breast tissue if the sensor feedback indicates that blood has ceased flowing through the breast. In this respect, the system 10 contains a built in failsafe mechanism that prevents over-compression to extent that could cause damage to a patient.

Referring once again to FIG. 1, in an embodiment, operation of the system 10 during the compression phase and the clamping phase may be controlled by the patient using switch controls 80, e.g., footswitch controls, such as disclosed in U.S. Pat. No. 10,004,470, which is hereby incorporated by reference herein in its entirety. Switch controls 80 are typically connected via a cable/wire 82 to mammography imaging system 10. The controls are also often mirrored on the opposite side of mammography imaging system 10 (not shown). Other controls (not shown) may be present on particular accessories placed either in the paddle/breast support area. In an embodiment, rather than being footswitch controls, the switch controls may be a handheld control unit 84 with a wired, wireless, Bluetooth or other connection with the system 10. In an embodiment, the patient may control the rate of compression and/or pressure or force applied during the compression phase and/or clamping phase using the switch controls. A feedback device, e.g. controller 32, may be configured to give feedback information about the image to obtain and may designed such that the feedback information is operatively perceivable by the patient (e.g., through an audible or visual indication). The feedback device, e.g., controller 32, may be configured to provide feedback information to the patient regarding the rate of compression (greater or lower rate of compression) and/or amount of pressure (higher or lower) required to produce an optimal image, in dependence upon the information received from the various sensor devices 54, 56, 58, 60. In this respect, the feedback device informs the patient when compression rate and/or pressure applied is sufficient to obtain a quality image, as determined from a blood pressure or other measurement taken from the patient through sensing devices 54, 56, 58, or 60, before or during the compression and/or clamping phase.

Figure 4:
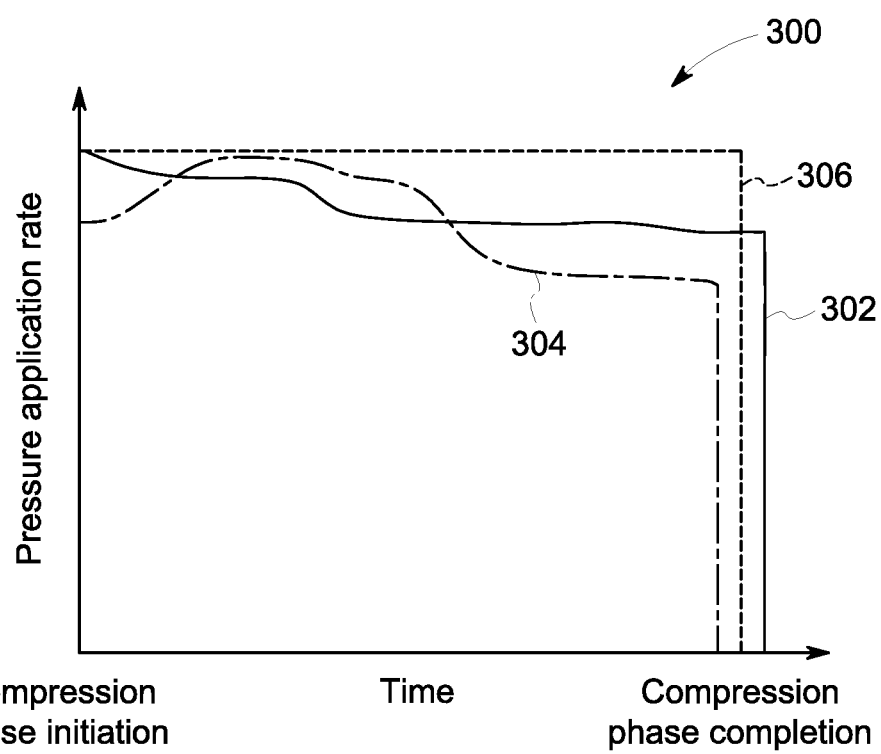
FIG. 4 is a graph illustrating pressure application rates during a compression phase of the system of FIG. 1.

Turning to FIG. 4, a graph 300 illustrating pressure application rates during the compression phase is depicted. Line 302 represents the pressure application rate change during the compression phase based on feedback from a blood pressure sensing device, as described above. As illustrated, the rate of pressure application and the final target force applied to the breast is varied in response to blood pressure measurements taken during the procedure. In this instance, the rate of applied pressure decreases throughout the compression phase with some periods of constant rate. In another implementation, such as that illustrated by line 304, the rate of pressure application initially increases before sharply dropping off. These two examples contrast with static techniques, represented by line 306, where the rate of pressure application and the final target pressure are fixed based on an initial blood pressure reading. As can be seen, therefore, by measuring blood pressure during the compression phase, a lower pressure application rate throughout the compression phase may be utilized, while still obtaining optimal image quality, which translates to greater patient comfort.

Figure 5:
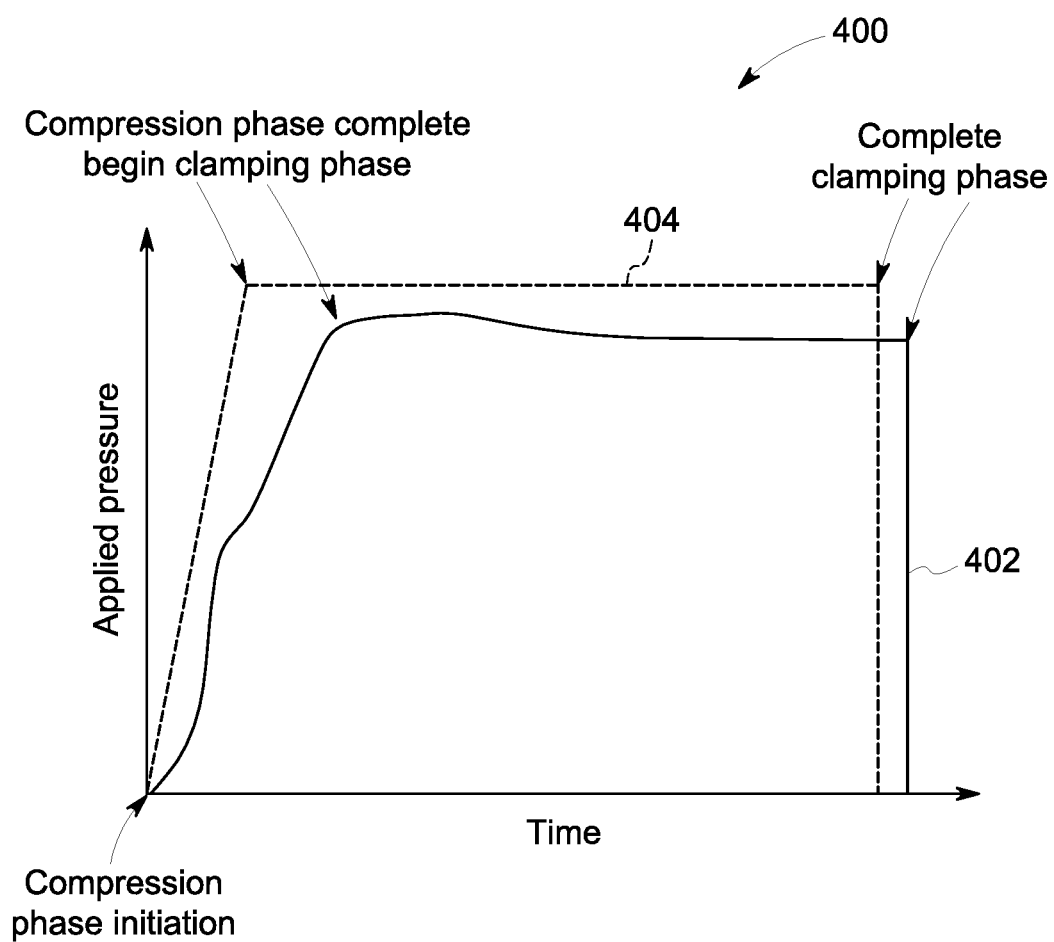
FIG. 5 is a graph illustrating applied pressure during a compression phase and a clamping phase of the system of FIG. 1.

FIG. 5 is a graph 400 illustrating applied pressure during a compression phase and a clamping phase for various imaging procedures. Line 402 shows the applied pressure during the compression phase and clamping phase are varied based on blood pressure measurements taken during both the compression phase and the clamping phase, as discussed above. In contrast, line 404 illustrates typical static techniques, which show that applied pressure increases at a uniform rate during the compression phase, and is held constant during the clamping phase. As illustrated, therefore, by measuring blood pressure continuously during the compression phase and clamping phase, lower applied pressures can be used while still obtaining optimal image quality which, again, translates to greater patient comfort.

In connection with the above, it is generally understood that better image quality can be achieved by flattening the breast to a greater degree, by applying a greater compressive force. Increased compressive force, however, is known to cause pain and discomfort for patients. By monitoring a patient's blood pressure during the compression and clamping phases, the system 10 is able to optimize the compressive force applied and/or the rate of compression to minimize patient discomfort while also ensuring that a minimum level of compression is achieved to ensure that quality images can be obtained. In embodiments, the feedback from the various sensing devices allows for automated, real-time changes in compression based on factors that ensure optimal image quality while at the same time reducing the pain experienced during the procedure.

In addition to being able to acquire physiological data directly for use in controlling and optimizing breast compression to improve imaging and minimize patient discomfort, the acquired physiological data may be read directly into a patient medical record along with other data collected by the system 10, without requiring separate measurements by the operator or clinician. Accordingly, by utilizing the system 10, the overall length of the mammography procedure and the associated time required for preparation may be shortened.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

In an embodiment, a mammography apparatus is provided. The mammography apparatus includes a support plate for supporting a breast of a patient, a compression plate movable toward and away from the support plate for compressing the breast against the support plate, and a controller configured to control movement of the compression plate toward and away from the support plate. The controller is configured to adjust at least one of a rate of compression and/or a pressure applied to the breast based on a measurement of a diastolic pressure and/or a systolic pressure of the patient. In an embodiment, the measurement of the diastolic pressure and/or the systolic pressure is taken during at least one of a compression phase and/or a clamping phase of the mammography apparatus. In an embodiment, the controller is configured to adjust in real time at least one of the rate of compression and/or the pressure applied to the breast based on a plurality of measurements the diastolic pressure and/or the systolic pressure of the patient taken during at least one of the compression phase and/or the clamping phase of the mammography apparatus. In an embodiment, the pressure is at least one of a target maximum pressure or a clamping phase pressure. In an embodiment, the apparatus includes a sensor device configured to measure the diastolic pressure and/or the systolic pressure. In an embodiment, the sensor device is configured for placement on a body part of the patient not undergoing compression. The sensor device may be integrated within one of the support plate or the compression plate. In some embodiments, the sensor device is at least one of an ultrasound device, and/or automated cuff or a thermal imaging device. In an embodiment, the measurement is a continuous measurement taken during at least one of the compression phase and/or the clamping phase. In an embodiment, the controller is configured to adjust the at least one of the rate of compression and the pressure applied to the breast based on at least one of a measured size and a measured volume of the breast. In an embodiment, the apparatus may include at least one of a blood oxygen sensor and/or a temperature sensor integrated with at least one of the support plate or the compression plate, wherein the controller is further configured to adjust at least one of the rate of compression and/or the pressure applied to the breast based on a measured blood oxygen content or body temperature. In an embodiment, the controller is further configured to cease movement of the compression plate to cease and/or reduce compression of the breast when a target tissue density or target tissue rigidity is detected. In an embodiment, the controller is further configured to automatically cease and/or reduce compression of the breast if a stoppage in a flow of blood in the breast is detected. In an embodiment, the apparatus includes a radiation source for applying radiation to the breast.

In another embodiment, a diagnostic imaging apparatus is provided. The apparatus includes a support plate for supporting tissue of a patient, a compression plate movable toward and away from the support plate for compressing the tissue against the support plate, and a controller configured to control movement of the compression plate toward and away from the support plate, and to adjust in real time at least one of a rate of compression and/or a pressure applied to the tissue based on a measurement of a physiological parameter of a patient taken during at least one of a compression phase and/or a clamping phase of the apparatus. In an embodiment, the controller allows a patient to control movement of the compression plate toward and away from the support plate to adjust the rate of compression and/or the pressure applied to the tissue based upon feedback provided by the apparatus regarding the measurement of the physiological parameter taken during at least one of a compression phase and/or a clamping phase. In an embodiment, the apparatus includes a patient-controllable switch operable to control movement of the compression plate toward and away from the support plate. In an embodiment, the physiological parameter is one of a diastolic pressure or a systolic pressure of the patient. In an embodiment, the controller is configured to adjust the at least one of the rate of compression and/or the pressure applied to the tissue based on at least one of a measured size and/or a measured volume of the tissue.

In yet another embodiment, a method of operating a mammography apparatus is provided. The method includes the steps of positioning a breast of a patient on a support plate, moving a compression plate towards the support plate to compress the breast of a patient, measuring a diastolic pressure and/or a systolic pressure of a patient, and varying at least one of a rate of compression and/or a pressure applied to the breast based on the measurement the diastolic pressure and/or the systolic pressure. In an embodiment, the step of measuring includes continuously measuring the diastolic pressure and/or the systolic pressure throughout a compression phase of the apparatus. In an embodiment, the step of measuring is carried out utilizing a sensor device integrated with one of the support plate and the compression plate. In an embodiment, the method may also include determining at least one of a size and/or a volume of the breast, and varying at least one of the rate of compression and/or the pressure applied to the breast based on the at least one of the size and/or the volume of the breast.

While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A mammography apparatus, comprising:
a support plate for supporting a breast of a patient;
a compression plate movable toward and away from the support plate for compressing the breast against the support plate; and
a controller configured to control movement of the compression plate toward and away from the support plate, and to adjust at least one of a rate of compression and/or a pressure applied to the breast based on a measurement of a diastolic pressure and/or a systolic pressure of the patient;
wherein: the measurement of the diastolic pressure and/or the systolic pressure of the patient is taken during at least one of a compression phase and/or a clamping phase of the mammography apparatus; and
wherein: the controller is configured to continuously adjust in real-time at least one of the rate of compression and/or the pressure applied to the breast based on a plurality of measurements the diastolic pressure and/or the systolic pressure of the patient taken during at least one of the compression phase and/or the clamping phase of the mammography apparatus.

2. The mammography apparatus of claim 1, wherein: the pressure is at least one of a target maximum pressure and/or a clamping phase pressure.

3. The mammography apparatus of claim 1, further comprising: a sensor device configured to measure the diastolic pressure and/or the systolic pressure.

4. The mammography apparatus of claim 3, wherein: the sensor device is configured for placement on a body part of the patient not undergoing compression.

5. The mammography apparatus of claim 3, wherein: the sensor device is integrated within one of the support plate or the compression plate.

6. The mammography apparatus of claim 3, wherein: the sensor device is at least one of an ultrasound device, an automated cuff and/or a thermal imaging device.

7. The mammography apparatus of claim 3, wherein: the measurement is a continuous measurement taken during at least one of the compression phase and/or the clamping phase.

8. The mammography apparatus of claim 1, wherein: the controller is configured to adjust the at least one of the rate of compression and/or the pressure applied to the breast based on at least one of a measured size and/or a measured volume of the breast.

9. The mammography apparatus of claim 3, further comprising:
at least one of a blood oxygen sensor and a temperature sensor integrated with at least one of the support plate and/or the compression plate;
wherein the controller is further configured to adjust at least one of the rate of compression and/or the pressure applied to the breast based on a measured blood oxygen content or body temperature.

10. The mammography apparatus of claim 3, wherein:
the controller is further configured to cease compression of the breast when a target tissue density or target tissue rigidity is detected.

11. The mammography apparatus of claim 3, wherein:
the controller is further configured to reduce compression of the breast when a target tissue density or target tissue rigidity is detected.

12. The mammography apparatus of claim 3, wherein:
the controller is further configured to automatically cease and/or reduce compression of the breast if a stoppage in a flow of blood in the breast is detected.

13. The mammography apparatus of claim 1, further comprising: a radiation source for applying radiation to the breast.

14. A method of operating a mammography apparatus, comprising the steps of: positioning a breast of a patient on a support plate; moving a compression plate towards the support plate to compress the breast of a patient; measuring a diastolic pressure and/or a systolic pressure of a patient; and varying at least one of a rate of compression and/or a pressure applied to the breast based on the measurement of the diastolic pressure and/or the systolic pressure; wherein: the step of measuring includes continuously measuring the diastolic pressure and/or the systolic pressure throughout a compression phase of the apparatus.

15. The method according to claim 14, wherein: the step of measuring is carried out utilizing a sensor device integrated with one of the support plate and the compression plate.

16. The method according to claim 14, further comprising the steps of:
determining at least one of a size and/or a volume of the breast; and
varying at least one of the rate of compression and/or the pressure applied to the breast based on the at least one of the size and/or the volume of the breast.

* * * * *